United States Patent
Pulugurtha (12) 
(10) Patent No.: US 9,114,032 B1
(45) Date of Patent: Aug. 25, 2015

(54) METHOD OF MAKING A STENT

(71) Applicant: Medtronic Vascular, Inc., Santa Rosa, CA (US)

(72) Inventor: Syamala Rani Pulugurtha, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 14/283,895

(22) Filed: May 21, 2014

(51) Int. Cl.
*A61F 2/82* (2013.01)
*B23K 26/38* (2014.01)
*B29C 67/00* (2006.01)
*B22F 3/105* (2006.01)
*B22F 3/24* (2006.01)
*C23F 1/02* (2006.01)
*B33Y 10/00* (2015.01)
*B29K 101/12* (2006.01)
*B29L 31/00* (2006.01)

(52) U.S. Cl.
CPC .............. *A61F 2/82* (2013.01); *B22F 3/1055* (2013.01); *B22F 3/24* (2013.01); *B23K 26/38* (2013.01); *B29C 67/0066* (2013.01); *C23F 1/02* (2013.01); *B22F 2003/247* (2013.01); *B29K 2101/12* (2013.01); *B29K 2995/0056* (2013.01); *B29L 2031/7534* (2013.01); *B33Y 10/00* (2014.12)

(58) Field of Classification Search
None
See application file for complete search history.

(56) References Cited

U.S. PATENT DOCUMENTS

| | | | |
|---|---|---|---|
| 8,353,952 | B2 | 1/2013 | Thompson et al. |
| 2007/0061007 | A1 | 3/2007 | Nolting |
| 2011/0067778 | A1 | 3/2011 | Mitchell et al. |
| 2011/0070357 | A1 | 3/2011 | Mitchell et al. |
| 2011/0070358 | A1* | 3/2011 | Mauch et al. ............... 427/2.25 |
| 2012/0067454 | A1 | 3/2012 | Melder |
| 2012/0067455 | A1 | 3/2012 | Mitchell et al. |
| 2012/0070562 | A1 | 3/2012 | Avelar et al. |
| 2012/0070563 | A1 | 3/2012 | Mitchell et al. |
| 2013/0331927 | A1* | 12/2013 | Zheng et al. ............... 623/1.19 |
| 2014/0277375 | A1* | 9/2014 | Weier et al. ............... 623/1.15 |
| 2015/0010422 | A1* | 1/2015 | Nash .................................. 419/2 |

* cited by examiner

Primary Examiner — Anita Alanko (57) ABSTRACT

A method of making a stent includes a three-dimensional printer receiving a dataset corresponding to a three-dimensional precursor stent. The three-dimensional printer forms a precursor stent. The precursor stent comprises a plurality of bands disposed adjacent to each other, wherein each band comprises a plurality of struts connected by a plurality of crowns, and a plurality of connectors connecting each band to an adjacent band. The precursor stent is processed to remove a selected number of the plurality of connectors between adjacent bands such that at least one connector between each set of adjacent bands is removed. In an embodiment, only one connector remains between each adjacent band after the selected number of connectors have been removed.

19 Claims, 8 Drawing Sheets

METHOD OF MAKING A STENT

FIELD OF THE INVENTION

The invention relates generally to methods of making a stent, and more particularly to a method of making stents using rapid form prototyping or three-dimensional printing.

BACKGROUND OF THE INVENTION

A wide range of medical treatments exist that utilize stents or endoluminal prostheses. As used herein, the term "stent" is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, different stents have been developed, each providing a uniquely beneficial structure to modify the mechanics of the targeted lumen wall. For example, stent prostheses are known for implantation within body lumens to provide artificial radial support to the wall tissue, which forms the various lumens within the body, and often more specifically, for implantation within the blood vessels of the body.

Stents have been made by a variety of methods, including forming a wire into waveform and helically wrapping the waveform around a mandrel, removing material from a tubular cylinder such as by a laser to leave a stent (sometimes referred to as a tubular slotted stent or laser cut stent), and forming individual cylindrical components and attaching adjacent cylindrical components to each other to form a tube. Such methods can be laborious, expensive, and time-consuming. It would be desirable to use rapid prototyping methods, such as three-dimensional printing, to make stents. However, rapid prototyping methods, when making stents with conventional shapes described below, do not allow for gaps between crowns of adjacent cylindrical elements or bands. In many applications, such as coronary arteries, stents need to be very flexible. Stents with all of the crowns of adjacent bands attached to each other are not sufficiently flexible for coronary applications.

BRIEF SUMMARY OF THE INVENTION

Embodiments hereof relate to a method of making a stent. In an embodiment, the method includes a three-dimensional printer receiving a dataset corresponding to a three-dimensional precursor stent. The three-dimensional printer forms a precursor stent using three-dimensional printing. The precursor stent comprises a plurality of bands disposed adjacent to each other, wherein each band comprises a plurality of struts connected by a plurality of crowns, and a plurality of connectors connecting each band to an adjacent band. The precursor stent is processed to remove a selected number of the plurality of connectors between adjacent bands such that at least one connector between each set of adjacent bands is removed. In an embodiment, only one connector remains between each adjacent band after the selected number of connectors have been removed.

Embodiments hereof also relate to another method of making a stent wherein a three-dimensional printer receives a dataset corresponding to a three-dimensional stent. The three-dimensional printer forms a precursor stent using three-dimensional printing. The precursor stent comprises a plurality of bands disposed adjacent to each other, wherein each band comprises a plurality of struts connected by a plurality of crowns, and wherein each crown of each band is attached to a corresponding crown of an adjacent band by a connector. The precursor stent is processed to remove a selected number of the connectors between crowns of adjacent bands such that a gap is formed between the crowns of adjacent bands where the connectors were removed. At least one connector is removed between crowns each set of adjacent bands.

Embodiment hereof also relate to a method of making a stent wherein a three-dimensional printer received a dataset corresponding to a three-dimensional stent. A precursor stent is formed using three-dimensional printing. The precursor stent includes a plurality of bands disposed adjacent to each other, wherein each band comprises a plurality of struts connected by a plurality of crowns, and wherein each crown of each band is attached to a corresponding crown of an adjacent band by a connector such that the precursor stent includes a plurality of first connectors made from a first material which are configured to remain and a plurality of second connectors made from a second material which are configured to be removed. The first material and second material are different materials. The precursor stent is processed to remove the plurality of second connectors without adversely affecting the bands and the plurality of first connectors. The step of processing the precursor stent to remove the plurality of second connectors may be chemical etching, wet chemical dissolution, solubilization, sublimation, and melting.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

Figure 1:
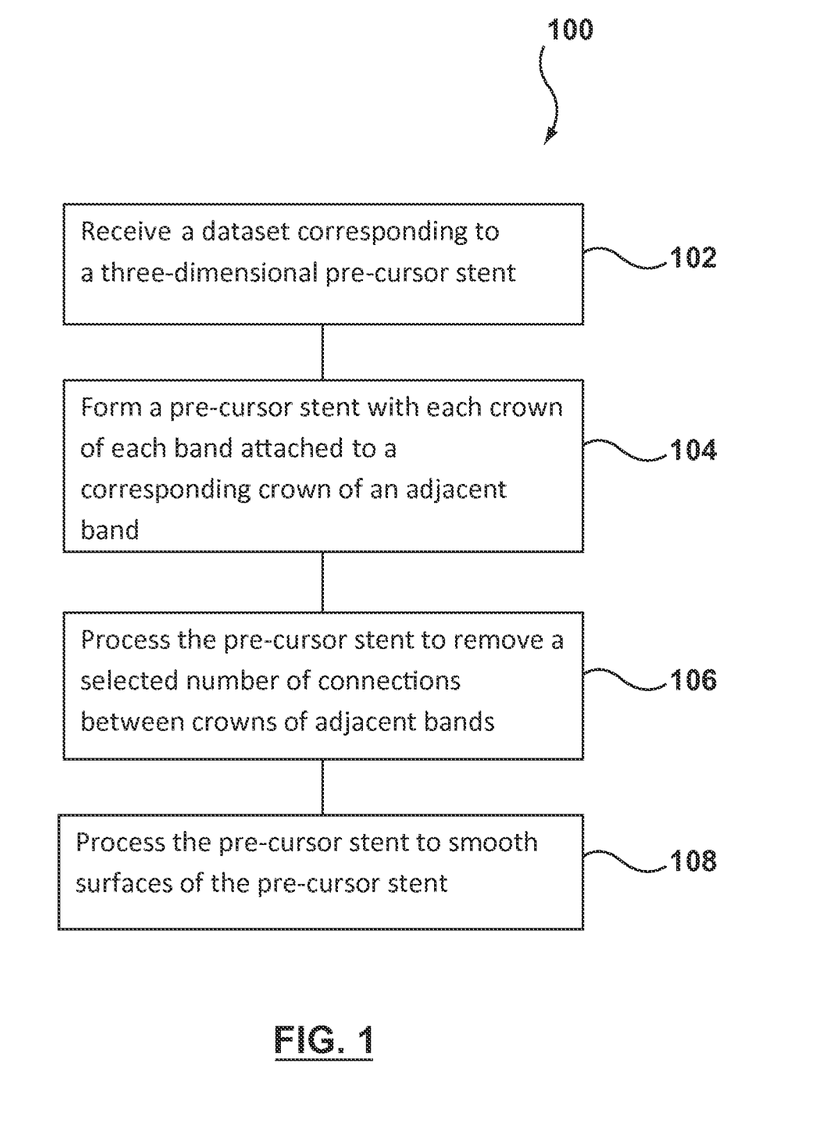
FIG. 1 is a flow chart showing steps in an embodiment of a method of making a stent.
Figure 4:
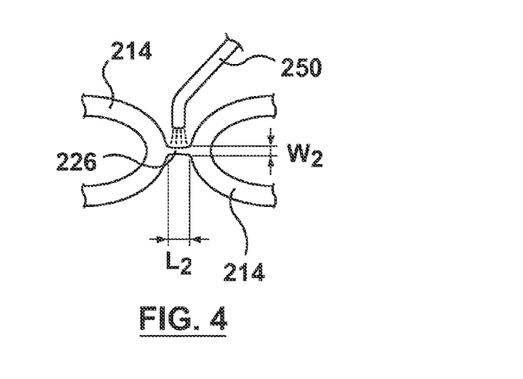
FIG. 4 is a close-up schematic view of an embodiment of another connector between crowns of adjacent bands of the precursor stent of FIG. 2 taken at area "B" of FIG. 2.
Figure 5:
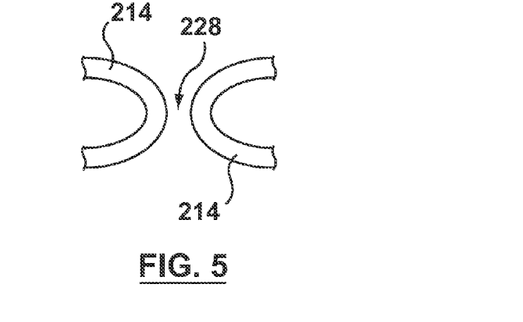
FIG. 5 is a close-up schematic view of the crowns of FIG. 4 with the connector removed after a step of the method of FIG. 1.
Figure 6:
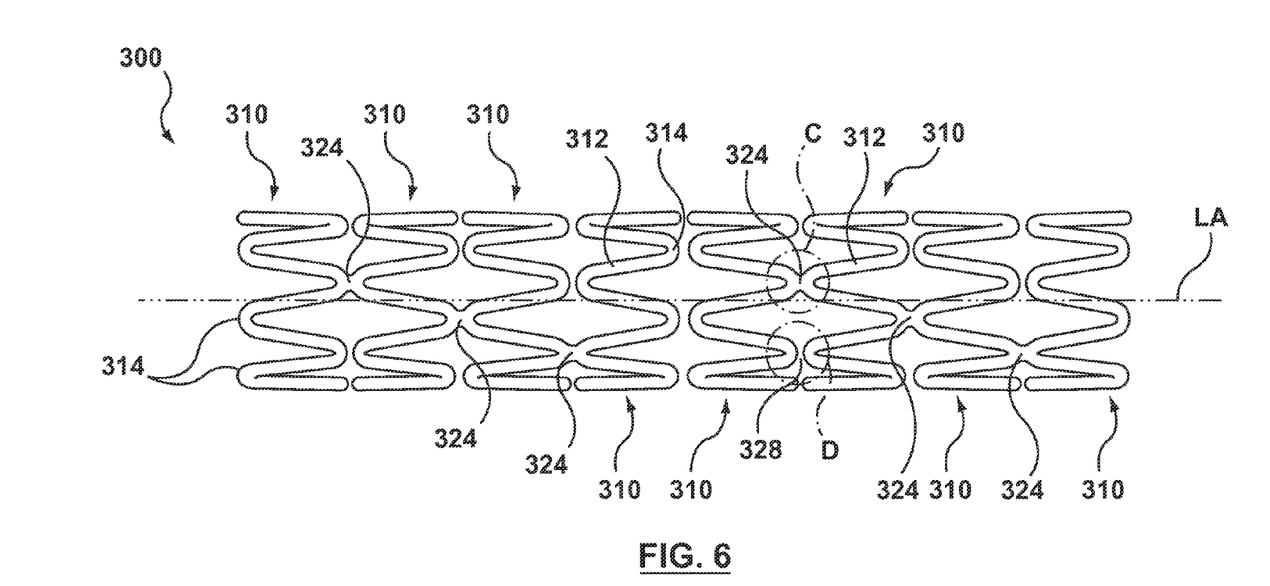
FIG. 6 is schematic side view of an embodiment of a stent made using the method of FIGS. 1-5.
Figure 7:
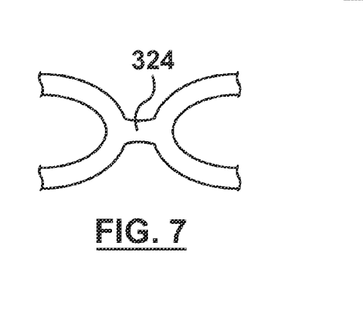
FIG. 7 is a close-up schematic view of an embodiment of a connector between crowns of adjacent bands of the stent of FIG. 6 taken at area "C" of FIG. 6.
Figure 8:
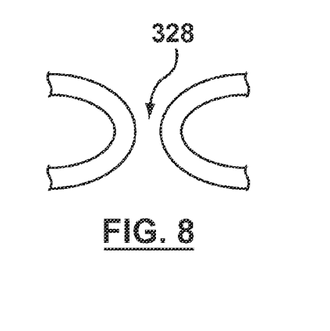
FIG. 8 is a close-up schematic view of an embodiment of a gap between crowns of adjacent bands of the stent of FIG. 6 taken at area "D" of FIG. 6.

FIG. 1 is a flow chart showing an embodiment of a method 100 of forming a stent. FIGS. 2-5 illustrate steps or details of steps in the method of FIG. 1. FIGS. 6-8 show an embodiment of a stent made according to the method of FIG. 1. The methods as described with respect to FIG. 1 are methods for making a stent using "three-dimensional printing" (3D printing) or "additive manufacturing" or "rapid prototyping". The term "three-dimensional printing" or "additive manufacturing" or "rapid prototyping" refers to a process of making a three-dimensional solid object of virtually any shape from a digital model. 3D printing is achieved using an additive process, where successive layers of material are laid down in different shapes. The terms, as used herein, may refer to methods such as, but not limited to, selective laser melting (SLM), direct metal laser sintering (DMLS), selective laser sintering (SLS), fused deposition modeling (FDM), and stereolithography (SLA). Further, any type of 3D printing machine that can print the materials described herein may be used Step 102 of FIG. 1 is for a 3D printer (not shown) to receive a dataset corresponding to a precursor stent 200 (shown in FIG. 2). In particular, the dataset is information regarding the characteristics of the precursor stent 200 from which the 3D printer can form precursor stent 200. For example, and not by way of limitation, the dataset may be a 3D printable file such as an STL file. STL (STereoLithography) is a file format native to the stereolithography CAD software created by 3D Systems. STL is also known as Standard Tessellation Language. This file format is supported by many software packages for use in 3D printing.

Figure 2:
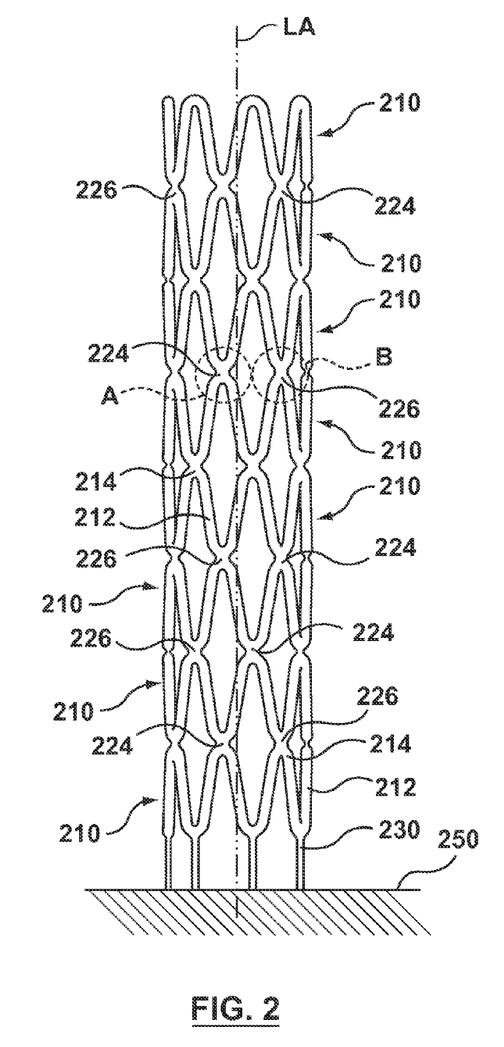
FIG. 2 is schematic side view of an embodiment of a precursor stent made in a step of the method of FIG. 1.

Step 104 of the method of FIG. 1 is for the 3D printing machine to form precursor stent 200. In step 104, the 3D printing machine lays down successive layers of a powder of the desired material to build precursor stent 200 from a series of cross sections. The material to form precursor stent 200 is the material desired for the finished stent, as described in more detail below. Examples of materials which may be 3D printed to form precursor stent 200 include, but are not limited to, stainless steel (such as "SS316L"), cobalt-chromium alloys, nickel titanium alloys such as Nitinol, magnesium and magnesium alloys, or combinations thereof. The term "cobalt-chromium" alloys as used herein includes alloys with cobalt and chromium. Generally, materials such as, but not limited to, cobalt-nickel-chromium alloys ("MP35N", "MP20N", and "MP35NLT") and chromium-nickel-tungsten-cobalt alloys ("L605") and cobalt-chromium-nickel-molybdenum alloys ("ELGILOY") are the types of materials included in the term "cobalt-chromium alloys" as used herein. Polymers may also be used to form precursor stent 200. Polymers which may be used to form precursor stent 200 include, but are not limited to, polylactide, poylglycolide, polysaccharides, proteins, polyesters, polyhydroxyalkanoates, polyalkelene esters, polyamides, polycaprolactone, polyvinyl esters, polyamide esters, polyvinyl alcohols, modified derivatives of caprolactonepolymers, polytrimethylene carbonate, polyacrylates, polyethylene glycol, hydrogels, photo-curable hydrogels, terminal diols, and combinations thereof.

Figure 3:
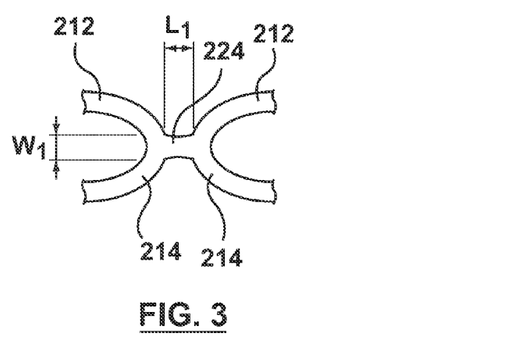
FIG. 3 is a close-up schematic view of an embodiment of a connector between crowns of adjacent bands of the precursor stent of FIG. 2 taken at area "A" of FIG. 2.

FIG. 2 shows an embodiment of precursor stent 200. According to an embodiment hereof, precursor stent 200 is 3D printed such that precursor stent 200 is built vertically on a substrate or surface 250. Substrate 250 may be any material suitable to be used in the environment of and with the materials used for the 3D printing process. As shown in FIG. 2, precursor stent 200 is built vertically from substrate 250. Precursor stent 200 includes a plurality of ring-shaped elements or bands 210. Bands 210 may also be referred to as cylindrical elements. In the embodiment of FIG. 2, precursor stent 200 includes eight bands 210; however, more or fewer bands 210 may be utilized. Each band 210 is disposed adjacent to another band along a longitudinal axis LA to form a tube or cylinder. Each band 210 is a waveform formed from a plurality of struts 212 connected together by bends or crowns 214. Further, crowns 214 of adjacent bands 210 are connected to each other by connectors 224 or 226. Crowns 214 of adjacent bands 210 connected by connectors 224 are shown in FIG. 3 and crowns 214 of adjacent bands 210 connected by connectors 226 are shown in FIG. 4. Further, the first band 210 is separated from substrate 250 by stilts or connectors 230, as shown in FIG. 2.

Connectors 224 and 226 are distinguished from each other in that connectors 224 are configured to remain connecting adjacent crowns 214 to each other and connectors 226 are configured to be removable from precursor stent 200. Similarly, stilts 230 are configured to be removable from precursor stent 200 such that the band 210 closest to substrate 250 is not damaged when separating precursor stent 200 from substrate 250. In the embodiment shown in FIGS. 2-4, connectors 224 have a length $L_1$ and width $W_1$, with the length being the distance between the crowns of adjacent bands and the width being perpendicular to the length. Similarly, connectors 226 have a length $L_2$ and a width $W_2$. In the embodiment of FIGS. 2-4, $W_1$ is greater than $W_2$ such that there is less material to remove in subsequent steps described below, whereas $L_1$ and $L_2$ are approximately equal. In other embodiments, $W_1$ and $W_2$ may be approximately equal. In other embodiments $W_2$ is greater than $W_1$. Similarly, $L_1$ and $L_2$ may vary with respect to each other. Although a particular precursor stent 200 embodiment is shown in FIGS. 2-4, different precursor stents may be formed using 3D printing. For example, and not by way of limitation, additional connectors may be utilized, the bands may be slanted, different bands may have different features (such as different thicknesses), additional features such as surface features, notches, etc. may be added, and other stent design differences may be utilized which are capable of being made using 3D printing.

As explained above, each crown 214 of a band 210 is connected to a crown 214 of an adjacent band 210 by a connector 224, 226. However, as also explained above, for certain applications it would be desirable for some of the crowns 214 of a band to be independent or not connected to the corresponding crown 214 of an adjacent band 210. Connectors 226 cannot simply be excluded from precursor stent 200 when 3D printing precursor stent 200 because excluding such connectors 226 when building a precursor stent vertically on substrate 250 would result in instability between bands 210 during the 3D printing process. For example, and not by way of limitation, if only one connector 224 were 3D printed between the first band 210 and the second band 210, the second band 210 would tend to move towards the first band 210 at the crowns 214 without a connector due to gravity. Such a tendency would negatively impact the ability to build a stent with the desired characteristics. Accordingly, step 106 of the method 100 of FIG. 1 is to process precursor stent 200 to remove a selected number of connectors 226 between crowns 214 of adjacent bands 210. In this particular embodiment, connectors 226 are selected to be removed such that only a single connector 224 is disposed between each band 210 and its adjacent band. However, the number and type of connectors 226 to be removed can be selected depending on various factors including, but not limited to, the desired flexibility of the resulting stent. Connectors 226 may be removed by laser ablation as shown in FIG. 4, wherein a laser 250 removes connector 226. However, other methods to remove connectors 226 may be used, such as, but not limited to, chemical etching (as described in more detail below). Stilts 230 may be removed by methods similar to the methods for removing connectors 226. With connectors 226 removed, a gap 228 is disposed between crowns 214 of adjacent bands 210, as shown in FIG. 5.

In an embodiment, the dataset used for the 3D printer to build precursor stent 200 also provides information to assist in removing connectors 226. In particular, the dataset distinguishes between connectors 224 that are configured not to be removed and connectors 226 that are configured to be removable. Thus, in one embodiment, precursor stent 200, after being separated from substrate 250, may be placed on a rotatable and translatable mandrel. Based on information from the dataset, a "home" position is established, such as at the first connector 224 disposed between the first band 210 and the adjacent band 410. Based on the dataset, the mandrel is rotated to the appropriate coordinates for each connector 226. Thus, in an embodiment, the mandrel rotates and/or translates the precursor stent 200 from the "home" position to a position where the first connector 226 is in a position to be ablated by a laser ablation apparatus. With the mandrel at the location of the first connector 226, connector 226 may be laser ablated. Laser ablation may be accomplished manually or automatically. If done automatically, the laser ablation apparatus receives the dataset such that the 3D printing of connectors 226, rotation of the mandrel, and the laser ablation of connectors 226 are coordinated. In other words, the dataset identifies which connectors are connectors 226 as opposed to connectors 224. The mandrel places precursor stent in the proper location such that the laser is aligned with one of the connectors 226. The laser then ablates the connector 226. During the laser ablation, the mandrel may move such that the laser ablates all of connector 226. Upon completion of ablation of one of the connectors 226, the mandrel rotates and/or translates such that another connector 226 is aligned with the laser ablation apparatus. In another embodiment, instead of a mandrel rotating and translating to align the connectors with the laser ablation apparatus, the laser ablation apparatus may move to align itself with connectors 226.

In another embodiment, the processing of step 106 to remove connectors 226 may be accomplished by exposing precursor stent to a condition or material that removes connectors 226 without adversely affecting bands 210 and connectors 224. In such an embodiment, connectors 226 are made from a different material than bands 210 and connectors 224. Similarly, stilts 230 may be made from the same as connectors 226. Precursor stent 200 is then exposed to a condition or etchant such that connectors 226 (and stilts 230) are removed. For example, and not by way of limitation, step 106 may remove connectors 226 by chemical etching, wet chemical dissolution, solubilization, sublimation, or melting.

Accordingly, in one exemplary embodiment, a cobalt-chromium alloy is used as the material to 3D print bands 210 and connectors 224, while silver is used to 3D print connectors 226. Precursor stent 200 is exposed to nitric acid, which chemically etches the silver connectors 226 without harming the cobalt-chromium alloy bands 210 and connectors 224. Although a particular embodiment for the etchant and the materials of bands 210, connectors 224, and connectors 226 has been described, other materials and processes that permit building a precursor stent 200 with different a different material for connectors 226 and removal of connectors 226 without adversely affecting bands 210 and connectors 224 may also be used. For example, and not by way of limitation, the combinations of materials and etchants described in the chart below may be utilized.

| Etchant/process | Bands 210/connectors 224 | Connectors 226/stilts 230 |
| --- | --- | --- |
| Xenon-difluoride | Cobalt-chromium alloys (MP35N, MP20N, MP35NLT, L605, ELGILOY) | Tantalum, tungsten, molybdenum, niobium, rhenium, carbon, germanium, silicon, Ta-2.5 W |
| Nitric Acid, sulfuric acid | Cobalt-chromium alloys (MP35N, MP20N, MP35NLT, L605, ELGILOY), nickel-titanium alloys, Titanium, Titanium alloys | Copper |
| Nitric Acid | Cobalt-chromium alloys (MP35N, MP20N, MP35NLT, L605, ELGILOY), Nitinol, Titanium, Titanium alloys | Silver |
| Water, salt water | Cobalt-chromium alloys (MP35N, MP20N, MP35NLT, L605, ELGILOY), stainless steel, Nitinol, Titanium, Titanium alloys | zinc, magnesium, gold, silver, aluminum |

| Etchant/process | Bands 210/connectors 224 | Connectors 226/stilts 230 |
|---|---|---|
| Heat (separation via melt or sublimation) | Cobalt-chromium alloys (MP35N, MP20N, MP35NLT, L605, ELGILOY), stainless steel | zinc, magnesium |
| Xenon difluoride Dilute HF | Cobalt-chromium alloys (MP35N, MP20N, MP35 NLT, L605, ELGILOY | titanium, titanium alloys |

Step 108 of method 100 is to process precursor stent 200 to smooth surfaces of precursor stent 200. Some 3D printing machines form objects with coarse surfaces, burrs, and residue powder that are not sufficiently smooth for use as stents. Accordingly, step 108 may be electropolishing, laser micromachining, or other process to smooth the surfaces of precursor stent 200. Accordingly, struts 212 and crowns 214 of precursor stent 200 made in step 104 may be slightly thicker than the final desired thickness of these elements to account for processes to smooth or otherwise finish precursor stent 200 since such processes tend to be subtractive processes. Other finishing processes may be performed on precursor stent 200 to prepare precursor stent 200 for use in a body, such as, but not limited to, passivation and sterilization. Further processing may also include steps such as adding coatings to the stent, adding radiopaque markers, adding biologically or pharmaceutically active substances to the stent, and/or adding surface features (such as recesses) to the stent. Some of this described further processing may instead be included in step 104 of 3D printing the precursor stent. For example, and not by way of limitation, surface features such as recesses may be formed in the stent as part of the 3D printing process. Step 108 may be performed before or after step 106.

With method 100 completed, precursor stent 200 has been transformed to stent 300 shown in FIGS. 6-8. Stent 300 includes a plurality of ring-shaped elements or cylindrical elements or bands 310. In the embodiment of FIG. 6, stent 300 includes eight bands 310 corresponding to the eight bands 210 of precursor stent 200. However, more or less bands 310 may be utilized. Each band 310 is disposed adjacent to another band along a longitudinal axis LA to form a tube or cylinder. Each band 310 is a waveform formed from a plurality of struts 312 connected together by bends or crowns 314. At least one crown 314 of each band is connected to a corresponding crown 314 of an adjacent band 310 by connector 324. FIG. 7 shows a close up view of one connector 324 connecting crowns 314 of adjacent bands 310 to each other. At other crowns, a gap 328 is disposed between the crown 314 and the corresponding crown 314 of the adjacent band 310, as shown in FIG. 8.

Although the embodiments shown and described herein refer to a crown connected to a corresponding crown of an adjacent band on the precursor stent, other connections between adjacent bands may be used instead. For example, and not by way of limitation, a crown of one band may be connected to a strut of an adjacent band, or struts of adjacent bands may be connected. Further, connectors 224, 226 may be angled with respect to the longitudinal axis LA or may be curved.

In another embodiment, struts 312, crowns 314, and/or connectors 324 of stent 300 may be hollow such that they may be filled with a biologically or pharmacologically active substance, to be released upon deployment of stent 300 in the body lumen. In one embodiment, the members which are desired to be hollow, i.e., struts 212, crowns 214, and/or connectors 224 are formed hollow during the 3D printing of precursor stent 200. Accordingly, after the further processing described above, struts 312, crowns 314, and connectors 324 of the resulting stent will be hollow. Further steps of filling the lumen with a biologically or pharmacologically active substance, and providing openings in the struts 312, crowns 314, and/ connectors 324 may be performed as described below.

Figure 9:
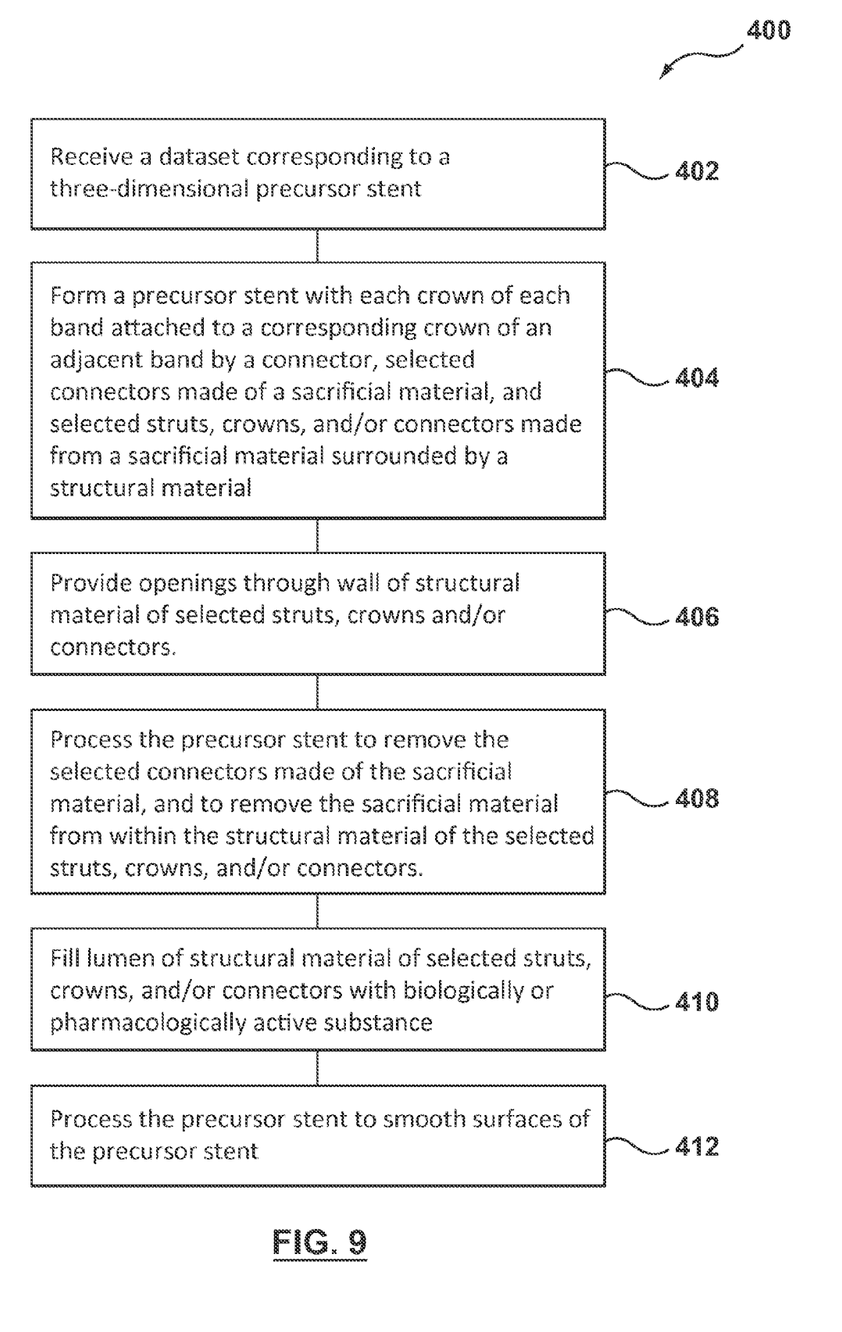
FIG. 9 is a flow chart showing steps in an embodiment of another method of making a stent.
Figure 15:
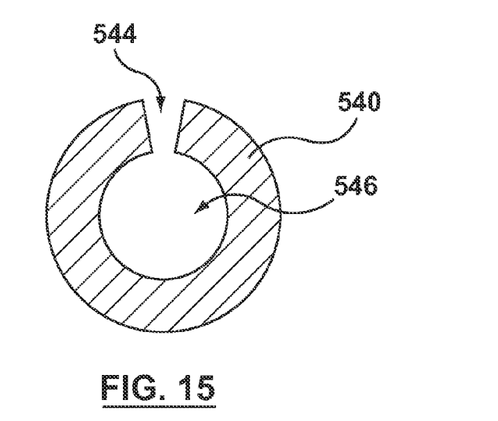
FIG. 15 is a cross-sectional view of the strut, crown, or connector of FIG. 11 after another step of the method of FIG. 9.
Figure 16:
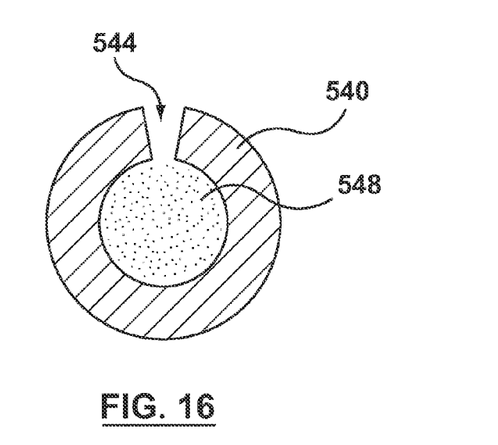
FIG. 16 is a cross-sectional view of one of the strut, crown, or connector of FIG. 11 after another step of the method of FIG. 9.
Figures 17, 18, 19:
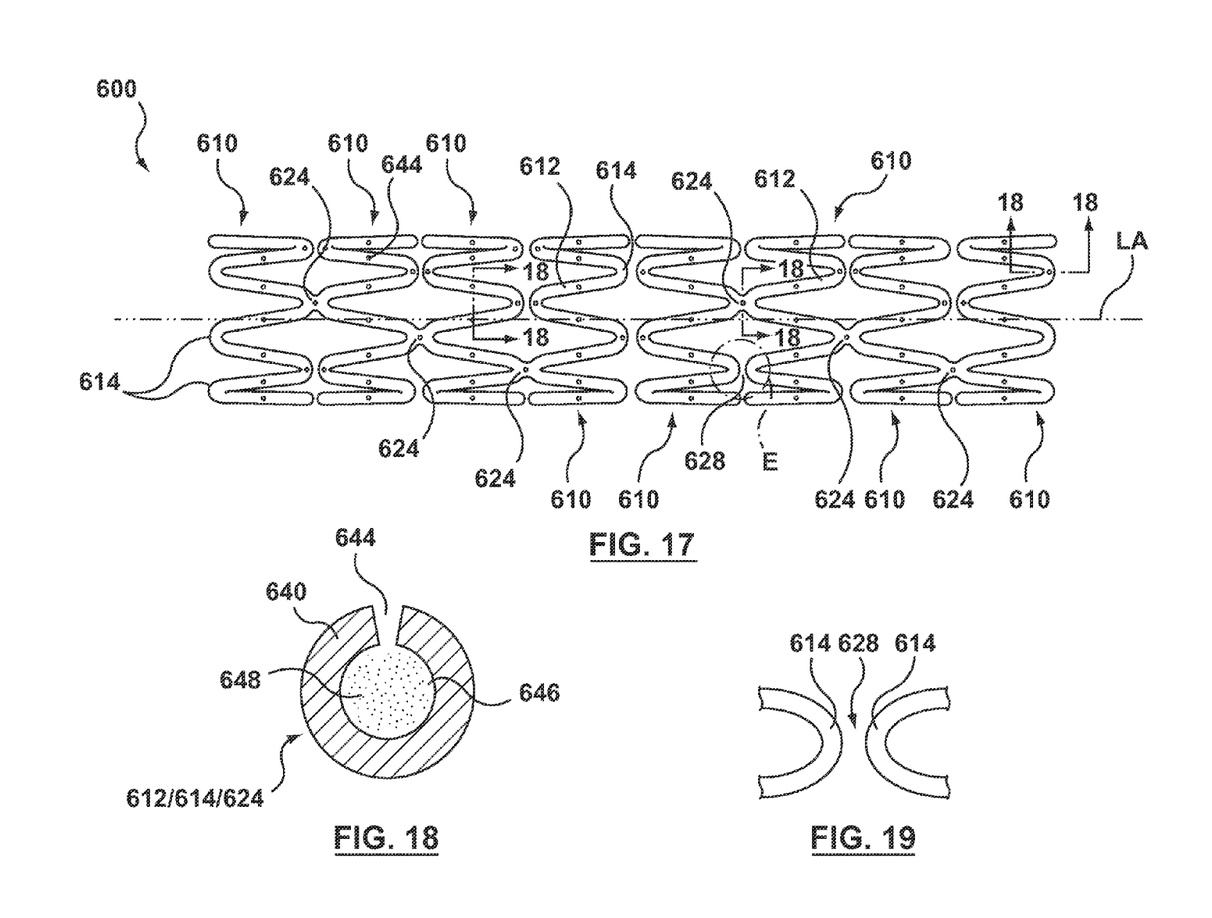
FIG. 17 is a schematic side view of an embodiment of a stent made using the method of FIGS. 9-14.
FIG. 18 is a schematic cross-sectional view of an embodiment of a strut, crown, or connector between crowns of adjacent bands of the stent of FIG. 17 taken along line 18-18 of FIG. 17.
FIG. 19 is a close-up schematic view of an embodiment of a gap between crowns of adjacent bands of the stent of FIG. 17 taken at area "E" of FIG. 17.

FIG. 9 is a flow chart showing an embodiment of another method 400 of forming a stent with hollow members, such as hollow struts, crowns, and/or connectors, as described in more detail below. FIGS. 10-16 illustrate steps or details of steps in the method of FIG. 9. FIGS. 17-19 show an embodiment of a stent made according to the method of FIG. 9. The methods as described with respect to FIG. 9 are methods for making a stent using "three-dimensional printing" (3D printing) or "additive manufacturing" or "rapid prototyping". The term "three-dimensional printing" or "additive manufacturing" or "rapid prototyping" refers to a process of making a three-dimensional solid object of virtually any shape from a digital model. 3D printing is achieved using an additive process, where successive layers of material are laid down in different shapes. The terms, as used herein, may refer to methods such as, but not limited to, selective laser melting (SLM), direct metal laser sintering (DMLS), selective laser sintering (SLS), fused deposition modeling (FDM), and stereolithography (SLA). Further, any type of 3D printing machine that can print the materials described herein may be used Step 402 of FIG. 1 is for a 3D printing machine (not shown) to receive a dataset corresponding to a precursor stent 500 (shown in FIG. 10). In particular, the dataset is information regarding the characteristics of the precursor stent 500 from which the 3D printer can form precursor stent 500. For example, and not by way of limitation, the dataset may be a 3D printable file such as an STL file. STL (STereoLithography) is a file format native to the stereolithography CAD software created by 3D Systems. STL is also known as Standard Tessellation Language. This file format is supported by many software packages for use in 3D printing.

Step 404 of the method of FIG. 9 is for the 3D printing machine to form precursor stent 500. In step 404, the 3D printing machine lays down successive layers of a powder of the desired materials to build precursor stent 500 from a series of cross sections. The materials used to form precursor stent 500 in this embodiment include the material desired for the finished stent (also referred to as a "structural material") and a sacrificial material, as described in more detail below. Examples of structural materials which may be 3D printed to form precursor stent 500 include, but are not limited to, stainless steel (such as "SS316L"), cobalt-chromium alloys, nickel titanium alloys such as Nitinol, magnesium and magnesium alloys, or combinations thereof. The term "cobalt-chromium" alloys as used herein includes alloys with cobalt and chromium. Generally, materials such as, but not limited to, cobalt-nickel-chromium alloys ("MP35N", "MP20N", and "MP35NLT") and chromium-nickel-tungsten-cobalt alloys ("L605") and cobalt-chromium-nickel-molybdenum alloys ("ELGILOY") are the types of materials included in the term "cobalt-chromium alloys" as used herein. Polymers may also be used as structural materials to form precursor stent 500. Polymers which may be used to form precursor stent 500 include, but are not limited to, polylactide, poylglycolide, polysaccharides, proteins, polyesters, polyhydroxyalkanoates, polyalkelene esters, polyamides, polycaprolactone, polyvinyl esters, polyamide esters, polyvinyl alcohols, modified derivatives of caprolactonepolymers, polytrimethylene carbonate, polyacrylates, polyethylene glycol, hydrogels, photo-curable hydrogels, terminal diols, and combinations thereof.

Figure 10:
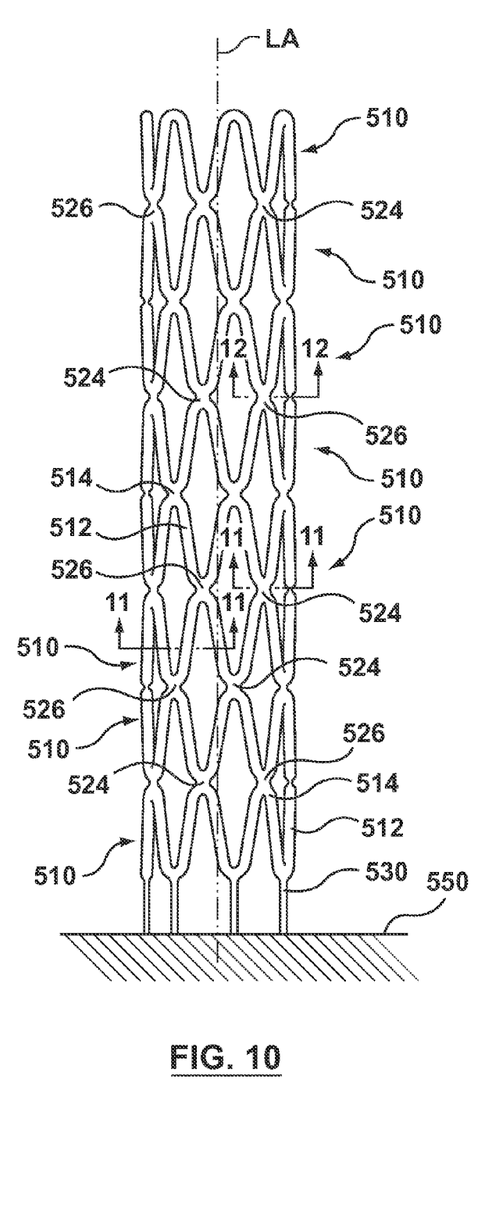
FIG. 10 is schematic side view of an embodiment of a precursor stent made in a step of the method of FIG. 9.

FIG. 10 shows an embodiment of precursor stent 500. According to an embodiment hereof, precursor stent 500 is 3D printed such that precursor stent 500 is built vertically on a substrate or surface 550. Substrate 550 may be any material suitable to be used in the environment of and with the materials used for the 3D printing process. As shown in FIG. 10, precursor stent 500 is built vertically from substrate 550. Precursor stent 500 includes a plurality of ring-shaped elements or bands 510. Bands 510 may also be referred to as cylindrical elements. In the embodiment of FIG. 10, precursor stent 500 includes eight bands 510; however, more or fewer bands 510 may be utilized. Each band 510 is disposed adjacent to another band along a longitudinal axis LA to form a tube or cylinder. Each band 510 is a waveform formed from a plurality of struts 512 connected together by bends or crowns 514. Further, crowns 514 of adjacent bands 510 are connected to each other by connectors 524 or 526, as described above.

Figure 11:
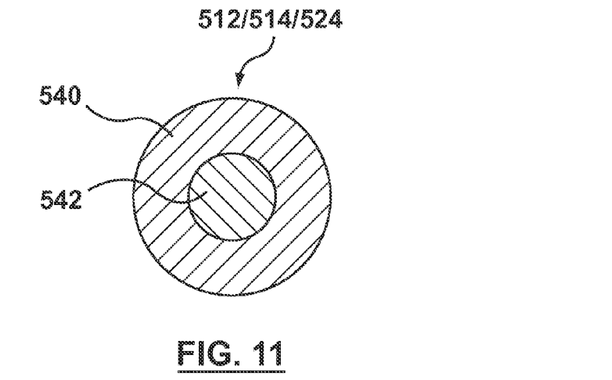
FIG. 11 is a schematic cross-sectional view of a strut, crown, or connector selected to remain taken along line 11-11 of FIG. 10.

In the present embodiment, it is desirable that at least some elements of the stent are hollow. Accordingly, FIG. 11 shows a schematic sectional view through a strut 512, crown 514, and/or connector 524 which is a selected connector to remain after processing described below. Although FIG. 11 and the subsequent steps described herein are directed to struts 512, crowns, 514, and connectors 524, the members selected to be hollow can be varied, while other members (i.e., struts, crowns, and/or connectors) may be selected to be made solid as described above with respect to connectors 224. Accordingly, all or some of the struts 512, crowns 514, and connectors 524 may be constructed to be made hollow as described herein. For example, and not by way of limitation, in one embodiment, struts 514 and crowns 514 are constructed to be made hollow as described herein, while connectors 524 are solid. In another embodiment, only connectors 524 are constructed to be made hollow. In another embodiment, certain bands 510 include struts 512 and crowns 514 constructed to be made hollow, while other bands 510 include solid struts 512 and crowns 514. For example, and not by way of limitation, the end-most bands 510 of each end of precursor stent 500 may include solid struts 512 and crowns 514, while the bands 510 towards the center of precursor stent 500 includes struts 512 and crowns 514 constructed to be made hollow. Other variations and embodiments of hollow and solid struts, crowns, and connectors are also contemplated.

FIG. 11 shows a schematic cross-sectional view of struts 512, crowns 514, and/or connectors 524 constructed to be made hollow. In particular, the 3D printing machine prints an outer member 540 made from a structural material surrounding an inner member 542 made from a sacrificial material. The selection of structural materials and sacrificial materials is described in more detail below.

Figure 12:
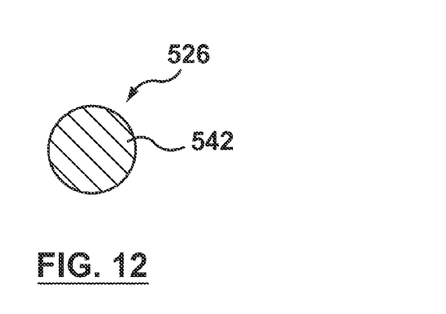
FIG. 12 is a schematic cross-sectional view of a connector selected to be removed taken along line 12-12 of FIG. 10.

FIG. 12 shows a schematic cross-sectional view of connectors 526 of precursor stent 500 taken along line 12-12 of FIG. 10. Connectors 526 are constructed to provide support between adjacent bands 510 of precursor stent 500 while precursor stent 500 is being 3D printed, but connectors 526 are configured to be removed. In this particular embodiment, connectors 526 are made from a sacrificial material, as described in more detail below.

Figure 14:
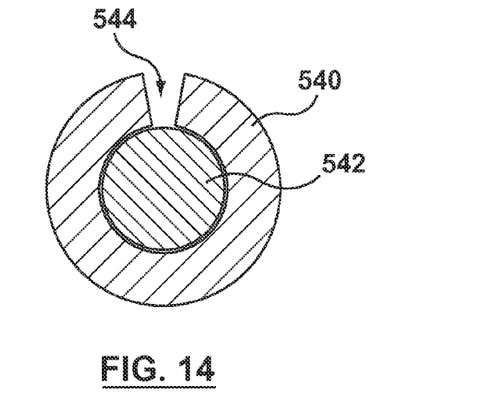
FIG. 14 is cross-sectional view of one of a strut, crown, or connector of FIG. 11 after a step of the method of FIG. 9.
Figure 14A:
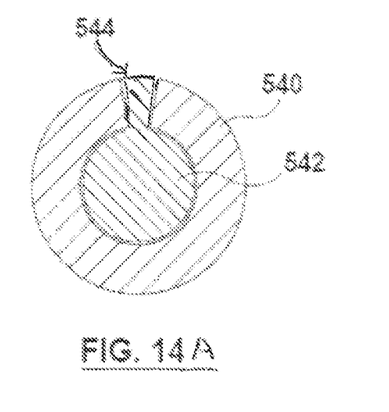
FIG. 14A is a cross-sectional view of another embodiment of a strut, crown, or connector of FIG. 11.

Step 406 shown in FIG. 9 is to provide openings 544 through outer member 540 at struts 512, crowns 514, and/or connectors 524 constructed to be made hollow. FIG. 14 shows the step of providing openings through outer member 540. Openings 544 may be laser cut, drilled, etched, or otherwise provided through outer member 544, and openings 544 may be a variety of shapes, such as circular or oval, and a variety of sizes. For example, and not by way of limitation, the step of 3D printing precursor stent 500 may include openings 544 provided at locations where it is desirable for a biologically or pharmacologically active substance to be eluted, as described in more detail below. Step 406 need not be performed after step 404, nor before step 408, although it is preferred to be before step 408, as explained in more detail below. In another example, and not by way of limitation, openings 544 may be formed by having outer member 540 formed around inner member 542 at the location of openings 544, as shown in FIG. 14A. In other words, at the location of each opening 544, inner member 542 is formed as extending into outer member 540, as shown in FIG. 14A. Accordingly, when inner member 542 is removed as described below, opening 544 is created and extends through outer member 540 to be in communication with a lumen 546.

Step 408 is to process pre-cursor stent 500 to remove connectors 526 and to remove inner member 542 at struts 512, crowns 514, and connectors 524 selected to be hollow, without adversely affecting outer member 540. Step 408 can be performed by any suitable process for removing connectors 526 and inner member 542 while preserving outer member 540. Accordingly, in one exemplary embodiment, a cobalt-chromium alloy is used as the material to 3D print outer member 540, while silver is used to 3D print inner member 542 and connectors 526. Precursor stent 500 is exposed to nitric acid, which chemically etches/removes the silver connectors 526 and inner member 542, without harming the cobalt-chromium alloy outer member 542. As explained above, all or some of struts 512, crowns 514, and connectors 524 may include an outer member 540 and an inner member 542 prior to exposure to the etchant. Any of the struts 512, crowns 514, and connectors 524 which do not include an outer member and an inner member, may be made solid with the same material as outer member 540. Although a particular embodiment for the etchant and the materials of outer member 540, inner member 542, and connectors 526 has been described, other materials and processes that permit building a precursor stent 500 with a sacrificial material for connectors 526 and inner member 540, and removal of such sacrificial material without adversely affecting the structural material of struts 512, crowns 514, and connectors 524 may also be used. For example, and not by way of limitation, the combinations of materials and etchants described in the chart below may be utilized. Stilts 530 may also be made from the sacrificial material to be removed during step 408.

| Etchant/process | Structural Material | Sacrificial Material |
| --- | --- | --- |
| Xenon-difluoride | Cobalt-chromium alloys (MP35N, MP20N, MP35NLT, L605, ELGILOY) | Tantalum, tungsten, molybdenum, niobium, rhenium, carbon, germanium, silicon, Ta-2.5 W |
| Nitric Acid, sulfuric acid | Cobalt-chromium alloys (MP35N, MP20N, MP35NLT, L605, ELGILOY), nickel-titanium alloys, Titanium, Titanium alloys | Copper |
| Nitric Acid | Cobalt-chromium alloys (MP35N, MP20N, MP35NLT, L605, ELGILOY), Nitinol, Titanium, Titanium alloys | Silver |
| Water, salt water | Cobalt-chromium alloys (MP35N, MP20N, MP35NLT, L605, ELGILOY), stainless steel, Nitinol, Titanium, Titanium alloys | zinc, magnesium, gold, silver, aluminum |
| Heat (separation via melt or sublimation) | Cobalt-chromium alloys (MP35N, MP20N, MP35NLT, L605, ELGILOY), stainless steel | zinc, magnesium |
| Xenon difluoride Dilute HF | Cobalt-chromium alloys (MP35N, MP20N, MP35 NLT, L605, ELGILOY | titanium, titanium alloys |

Figure 13:
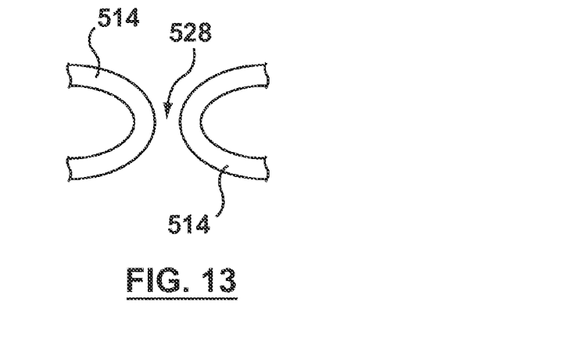
FIG. 13 is a close-up schematic view of the crowns of FIG. 10 where a connector selected to be removed has been removed after a step of the method of FIG. 9.

Upon completion of step 408, a gap 528 is created between crowns 514 of adjacent bands 510 where connectors 526 have been removed, as shown in FIG. 13. Further, at struts 512, crowns 514, and/or connectors 524 selected to be hollow, the lumen 546 of outer member 540 is created where inner member 542 has been removed, as shown in FIG. 15.

While it has been explained that openings 544 may be created after step 408, it may be desirable to have openings 544 prior to step 408 such that the etchant can more quickly reach different areas of precursor stent 500 where inner member 542 is to be removed. However, as explained above, this is not necessary.

After inner member 542 has been removed, a biologically or pharmacologically active substance 548 may be injected into lumen 546 of outer member 540, as shown in step 410 of FIG. 9. This produces an outer member 540 with a biologically or pharmacologically active substance 548 filling lumen 546, and openings 544 through which biologically or pharmacologically active substance 548 may be eluted, as shown in FIG. 16. Filling lumen 546 with a biologically or pharmacologically active substance may be accomplished by any suitable means. For example, and not by way of limitation, methods for filling lumens of hollow members described in U.S. Application Publication Nos. 2011/0070357; 2011/0067778; 2012/0067454; 2012/0067455; 2012/0070562; and 2012/0070563, each assigned to Medtronic Vascular, Inc., and each of which is incorporated by reference herein in its entirety.

Biologically or pharmacologically active substance 548 may include, but is not limited to, biologoicantineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other biologically or pharmacologically active substances or agents that may be used include nitric oxide, alpha-interferon, genetically engineered epithelial cells, and dexamethasone. In other examples, the biologically or pharmacologically active substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing biologically or pharmacologically active substances are well-known to those of ordinary skill in the art, the biologically or pharmacologically active substances are provided by way of example and are not meant to be limiting. Other biologically or pharmacologically active substances are equally applicable for use with the disclosed methods and compositions.

Further, a carrier may be used with the biologically or pharmacologically active substance 548. Examples of suitable carriers include, but are not limited to, ethanol, acetone, tetrahydrofuran, dymethylsulfoxide, a combination thereof, or other suitable carriers known to those skilled in the art. Still further, a surfactant may be formulated with the biologically or pharmacologically active substance and the solvent to aid elution of the biologically or pharmacologically active substance.

Step 412 of method 400 is to process precursor stent 500 to smooth surfaces of precursor stent 500. Some 3D printing machines form objects with coarse surfaces, burrs, and residue powder that are not sufficiently smooth for use as stents. Accordingly, step 512 may be electropolishing, laser micromachining, or other process to smooth the surfaces of precursor stent 500. Accordingly, struts 512, crowns 514, and connectors 524 of precursor stent 500 made in step 404 may be slightly thicker than the final desired thickness of these elements to account for processes to smooth or otherwise finish precursor stent 500 since such processes tend to be subtractive processes. Other finishing processes may be performed on precursor stent 500 to prepare precursor stent 500 for use in a body, such as, but not limited to, passivation and sterilization. Step 412 may be performed before or after step 410.

With method 400 completed, precursor stent 500 has been transformed to stent 600 shown in FIGS. 17-19. Stent 600 includes a plurality of ring-shaped elements or cylindrical elements or bands 610. In the embodiment of FIG. 17, stent 600 includes eight bands 610 corresponding to the eight bands 510 of precursor stent 500. However, more or less bands 610 may be utilized. Each band 610 is disposed adjacent to another band along a longitudinal axis LA to form a tube or cylinder. Each band 610 is a waveform formed from a plurality of struts 612 connected together by bends or crowns 614. At least one crown 614 of each band is connected to a corresponding crown 614 of an adjacent band 610 by connector 624.

FIG. 18 shows a schematic cross-sectional view of struts 612, crowns 614, and/or connectors 524 selected to be hollow taken along lines 18-18 in FIG. 17. As can be seen in FIGS. 17-18, such struts 612, crowns 614, and/or connectors 624 include an outer member 640 including a lumen 646 filed with a biologically or pharmacologically active substance 648, as described above. Further, openings 644 are provided through outer member 640 where desired. The location and size of openings 644 may be varied depending on the desired elution rate, carried elution rate, location and/or order of elution, and other factors.

FIG. 19 shows a close up view of crowns 614 of adjacent bands 610 where a connector 526 of precursor stent 500 has been removed, thereby leaving a gap 628 disposed between the crown 614 and the corresponding crown 614 of the adjacent band 610.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method of making a stent comprising the steps of:
receiving a dataset corresponding to a three-dimensional precursor stent;
forming a precursor stent using three-dimensional printing, wherein the precursor stent comprises a plurality of bands disposed adjacent to each other, wherein each band comprises a plurality of struts connected by a plurality of crowns, and a plurality of connectors connecting each band to an adjacent band;
processing the precursor stent to remove a selected number of the plurality of connectors between adjacent bands such that at least one connector between each set of adjacent bands is removed and a gap is formed between the crowns of adjacent bands where the selected number of the plurality of connectors were removed, wherein the selected number of the plurality of connectors are thinner than the connectors not removed.

2. The method of claim 1, wherein after the step of processing the precursor stent to remove the selected number of connectors at least one of the plurality of connectors remains between each set of adjacent bands.

3. The method of claim 1, wherein the step of removing the selected number of connectors comprises laser ablation of the connectors.

4. The method of claim 3, wherein the dataset includes information regarding which of the plurality of connectors are the selected number of the plurality of connectors, and wherein the step of removing the selected number of connectors by laser ablation includes a laser ablation apparatus receiving from the dataset locations for the plurality of selected connectors such that the laser ablations apparatus is sequentially aligned with each of the selected number of the plurality of connectors.

5. The method of claim 1, further comprising the step of processing the precursor stent to smooth surfaces of the precursor stent.

6. The method of claim 5, wherein the step of processing the precursor stent to smooth the surfaces comprises laser micro-machining or electropolishing.

7. The method of claim 1, wherein the step of forming a precursor stent comprises three-dimensional printing of a material comprising a metal material or a polymeric material.

8. The method of claim 6, wherein the material is a metal material and is selected from a group consisting of stainless steel, cobalt-chromium alloys, nickel titanium alloys, magnesium, and magnesium alloys.

9. The method of claim 6, wherein the material is a polymeric material and is selected from a group consisting of polylactide, poylglycolide, polysaccharides, proteins, polyesters, polyhydroxyalkanoates, polyalkelene esters, polyamides, polycaprolactone, polyvinyl esters, polyamide esters, polyvinyl alcohols, modified derivatives of caprolactonepolymers, polytrimethylene carbonate, polyacrylates, polyethylene glycol, hydrogels, photo-curable hydrogels, terminal diols, and combinations thereof.

10. A method of making a stent comprising the steps of:
receiving a dataset corresponding to a three-dimensional stent;
forming a precursor stent using three-dimensional printing, wherein the precursor stent comprises a plurality of bands disposed adjacent to each other, wherein each band comprises a plurality of struts connected by a plurality of crowns, and wherein each crown of each band is attached to a corresponding crown of an adjacent band by a connector such that the precursor stent includes a plurality of first connectors made from a first material which are configured to remain and a plurality of second connectors made from a second material which are configured to be removed, wherein the first material and the second material are different;

processing the precursor stent to remove the plurality of second connectors without adversely affecting the bands and the plurality of first connectors.

11. The method of claim 10, wherein the step of processing the precursor stent to remove the plurality of second connectors comprises exposing the precursor stent to a chemical etchant which etches the second material but does not etch the first material or adversely affect the plurality of bands.

12. The method of claim 11, wherein the plurality of bands are made from the first material.

13. The method of claim 10, wherein first material is selected from the group consisting of cobalt-chromium alloys, nickel-titanium alloys, titanium, and titanium alloys.

14. The method of claim 13, wherein the second material is copper or silver and the step of processing the precursor stent to remove the second connectors comprises exposing the precursor stent to nitric acid.

15. The method of claim 13, wherein the second material is copper and the step of processing the precursor stent to remove the second connectors comprises exposing the precursor stent to sulfuric acid.

16. The method of claim 10, wherein first material is a cobalt-chromium alloy, the second material is selected from the group consisting of tantalum, tungsten, molybdenum, niobium, rhenium, carbon, germanium, silicon, and Ta-2.5W, and wherein the step of processing the precursor stent to remove the second connectors comprises exposing the precursor stent to xenon-difluoride at low pressure and high temperature.

17. The method of claim 10, wherein the first material is selected from the group consisting of cobalt-chromium alloys, stainless steel, nickel-titanium alloys, titanium, and titanium alloys, the second material is selected from the group consisting of zinc, magnesium, gold, silver, and aluminum, and wherein the step of processing the precursor stent to remove the second connectors comprises exposing the precursor stent to water or salt water.

18. The method of claim 10, wherein the first material is a cobalt-chromium alloy or stainless steel, the second material is titanium or a titanium alloy, and wherein the step of processing the precursor stent to remove the second connectors comprises exposing the precursor stent to xenon-difluoride dilute HF.

19. The method of claim 10, wherein the first material is a cobalt-chromium alloy, the second material is zinc or magnesium, and wherein the step of processing the precursor stent to remove the second connectors comprises heating the precursor stent to melt or sublimate the second material without adversely affecting the first material.

* * * * *